United States Patent [19]

Reeve

[11] Patent Number: 5,210,094
[45] Date of Patent: May 11, 1993

[54] SULPHUR-BASED STABILIZERS FOR 3-ISOTHIAZOLONES

[75] Inventor: Paul F. D. Reeve, Le Plan de Grasse, France

[73] Assignee: Rohm and Haas Company, Philadelphia, Pa.

[21] Appl. No.: 674,832

[22] Filed: Mar. 25, 1991

[51] Int. Cl.$^5$ .............................. A01N 43/80
[52] U.S. Cl. ..................... 514/372; 518/213
[58] Field of Search ..................... 514/372; 548/213

[56] References Cited

U.S. PATENT DOCUMENTS

| | | | |
|---|---|---|---|
| 3,523,121 | 8/1970 | Lewis | 548/213 |
| 3,761,488 | 9/1973 | Lewis | 548/213 |
| 3,870,795 | 3/1975 | Miller | 548/213 |
| 4,067,878 | 1/1978 | Miller | 548/213 |
| 4,129,448 | 12/1978 | Greenfield | 548/213 |
| 4,150,026 | 4/1979 | Miller | 548/213 |
| 4,165,318 | 8/1979 | Greenfield | 548/213 |
| 4,241,214 | 12/1980 | Miller | 548/213 |
| 4,595,691 | 6/1986 | La Marre | 514/367 |
| 4,906,651 | 3/1990 | Hsu | 514/372 |
| 5,041,457 | 8/1991 | Hsu | 514/372 |

FOREIGN PATENT DOCUMENTS 315464 5/1989 European Pat. Off. .
342852 11/1989 European Pat. Off. .

OTHER PUBLICATIONS

Kathon 886 MW Microbicide and Kathon 893 MW Fungicide—Analysis in Metalworking Fluids by High Performance Liquid Chromatography 1988.

Primary Examiner—Robert Gerstl
Attorney, Agent, or Firm—Michael B. Fein

[57] ABSTRACT

A method of protecting 3-isothiazolones of the formula:

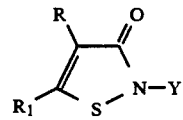

wherein Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloaklylamino, carbamoxy, or isothiazolonyl; an unsubstituted or halo-substituted $(C_2-C_8)$ alkenyl or alkynyl; a $(C_7-C_{10})$aralkyl optionally substituted with one or more of halogen, $(C_1-C_4)$alkyl or $(C_1-C_4)$alkoxy; and an aryl optionally substituted with one or more of halogen, nitro, $(C_1-C_4)$alkyl, $(C_1-C_4)$alkyl-acylamino, carb$(C_1-C_4)$alkoxy or sulfamyl; and R and $R^1$ is each independently H, halogen $(C_1-C_4)$ alkyl, $(C_4-C_8)$ cycloalkyl or joined together to form a phenyl; comprising incorporating therewith an effective amount of a sulphur-containing compound, or salt thereof, capable of reversibly forming an adduct with said isothiazolone. Stabilized isothiazolones and adducts with the sulfur-containing compound are also disclosed.

10 Claims, No Drawings

SULPHUR-BASED STABILIZERS FOR 3-ISOTHIAZOLONES

BACKGROUND OF THE INVENTION

1. Field of the Invention

This invention concerns the stabilization of 3-isothiazolone compounds, particularly in metal working fluid concentrates, by the incorporation with those compounds of certain sulphur-based compounds.

2. Description of the Prior Art

Isothiazolones have generated high commercial interest as microbicides to prevent spoilage of certain aqueous and non-aqueous products caused by microorganisms. They are highly effective microbicides (as used herein, "microbicides" includes bactericides, fungicides and algicides, and microbicidal activity is intended to include both the elimination of and the inhibition or prevention of growth of microbial organisms such as bacteria, fungi and algae). By suitable choice of functional groups, they are useful in a broad range of applications.

One significant area of application for isothiazolones is as microbicides in metal working fluids. Metal working fluids are proprietary combinations of chemicals, which may contain, inter alia, ingredients such as alkanolamines, pertroleum sulfonate surfactants, oils (napthenic, paraffinic, etc), chlorinated paraffins and fatty esters, sulfurized fatty compounds, phosphate esters, fatty acids and their amine salts, glycols, polglycols, boric acid esters and amides. They are utilized in the milling, machining, drilling, and other processing technologies for fabricating metal for the purposes of lubricating, cooling, preventing surface corrosion, and the like. They are sold in the form of active metal working fluid (MWF) concentrates, and are diluted in use to 1–10% active ingredients in water.

Because metal working fluids are recycled and stored, the growth of micro-organisms is favoured. Isothiazolones have been found effective in preventing the growth of such organisms. However, certain components in the metal working fluids tend to destroy the isothiazolone and so remove its microbicidal protective activity. This is a particular problem when the MWFs are in concentrate form. It has been found that even some other microbicides, present in combination with isothiazolones, may attack the isothiazolones. An example of this is the sodium salt of mescapto pyridine-N-oxide (sodium omadine), which has been found to remove 5-chloro-2-methyl isothiazolone from any system in which the two are present together.

Indeed, generally, it has long been recognized that either in storage prior to addition to a substrate to be treated or after addition, the efficacy of isothiazolones in many environments may be decreased because they are not stable under practical conditions of long term storage. Means have thus been sought for some time to improve the stability of isothiazolones.

U.S. Pat. Nos. 3,870,795 and 4,067,878 teach the stabilization of isothiazolones against chemical decomposition by addition of a metal nitrite or metal nitrate, but teach that other common metal salts, including carbonates, sulfates, chlorates, perchlorates, and chlorides are ineffective in stabilizing solutions of isothiazolones, such solutions usually being in water or in an hydroxylic solvent. U.S. Pat. Nos. 4,150,026 and 4,241,214 teach that metal salt complexes of isothiazolones are useful because they have enhanced thermal stability, while retaining biological activity.

It is known to use certain organic stabilizers for isothiazolones, generally for use situations where metal salts may create problems, such as corrosion, coagulation of latices, insolubility in non-aqueous media, interaction with the substrate to be stabilized, and the like. Formaldehyde or formaldehyde-releasing chemicals are known as stabilizers, (see U.S. Pat. Nos. 4,165,318 and 4,129,448), as are certain organic chemicals such as orthoesters (EP-A-315,464), epoxides (EP-A-342,852), and carbonyl compounds (copending European Application No. 90312417.0).

SUMMARY OF THE INVENTION

We have now discovered a class of compounds which provide considerable and surprising stability to isothiazolones against decomposition, particularly in MWF concentrates. In its broadest aspect therefore the invention provides a method of protecting against chemical degradation an isothiazolone of the formula:

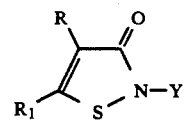

wherein Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloalkylamino, carbamoxy, or isothiazolonyl; an unsubstituted or halo-substituted $(C_2-C_8)$alkenyl or alkynyl; a $(C_7-C_{10})$aralkyl optionally substituted with one or more of halogen, $(C_1-C_4)$alkyl or $(C_1-C_4)$alkoxy; or an aryl optionally substituted with one or more of halogen, nitro, $(C_1-C_4)$alkyl, $(C_1-C_4)$alkyl-acylamino, carb$(C_1-C_4)$alkoxy or sulfamyl; and $R_1$ and R are each independently H, halogen, $(C_1-C_4)$alkyl, $(C_4-C_8)$ cycloalkyl or joined to form a phenyl; comprising incorporating therewith an effective amount of a sulphur-containing compound or salt thereof, capable of reversibly forming an adduct with said isothiazolone. It is believed that the sulphur-containing compounds of the present invention form hydrolysable adducts with isothiazolones; thus reversal of the adduct formation in such cases is by hydrolysis, usually accomplished through dilution. However, the invention is not limited to such cases.

DETAILED DESCRIPTION OF THE INVENTION AND PREFERRED EMBODIMENT

The invention provides a particularly advantageous form of protection, or stabilization. These stabilizers can be used to 'lock up' an isothiazolone, in the form of a stable adduct which is resistant to chemical degradation, and then when desired they can be made to 'release' the isothiazolone by reversing the adduct formation—usually simply by dilution of the product. Accordingly another aspect of the invention provides a compound comprising an adduct of an isothizolone as defined above and a sulphur-containing compound or salt thereof, wherein said adduct may be decomposed to release said isothiazolone. Preferably the adduct may be hydrolysed to release the isothiazolone.

In another aspect the invention provides a composition comprising an isothiazolone as defined above, a sulphur-containing compound as defined above, and optionally a solvent. In a further aspect the invention comprises the use of a sulphur-containing compound as previously defined to protect an isothiazolone against chemical degradation.

The stabilization discovered in the present invention is particularly surprising in view of the previously known incompatibility of 5-chloro-2-methyl isothiazolone and the sodium salt of 2-mercaptopyridine-N-oxide (sodium omadine), mentioned above. In the light of the present discovery it is now believed that the reason for the disappearance of the isothiazolone in that instance is because, as in the present invention, the sodium omadine forms an adduct with the isothiazolone. However, the adduct in that case is formed irreversibly so that the isothiazolone cannot be retrieved; the scope of the present invention covers only adducts whose formation is reversible.

The invention has particular value in the field of metal working fluids, which are commonly stored in concentrate form. Some of the components in MWFs are extremely aggressive towards isothizolones when in concentrate form, but of little threat when diluted to the normal use dilution. Thus the present invention can be employed by adding a stabilizer to protect the isothiazolones in the concentrate, the isothiazolone then being released automatically upon dilution by hydrolysis of the isothiazolone-stabilizer adduct.

The isothiazolones which are stabilized include those disclosed in U.S. Pat. Nos. 3,523,121 and 3,761,488 and represented by the formula:

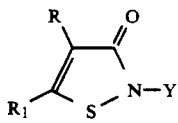

as defined above.

Preferred substituents for Y are substituted or unsubstituted ($C_1$–$C_{18}$) alkyl or ($C_3$–$C_{12}$) cycloalkyl; R is preferred to be H, or Me; and $R^1$ is preferred to be H. Representative of such preferred Y substituents are methyl, ethyl, propyl, isopropyl, butyl, hexyl, octyl, cyclohexyl, benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl, hydrogen, and the like.

Particularly preferred isothiazolones are 2-methyl-3-isothiazolone, and 2-n-octyl-3-isothiazolone.

Preferred stabilizers include compounds having a sulphur atom attached to a nitrogen-containing aromatic ring, in particular nitrogen-based heterocyclic thiols; especially preferred are: 2-mercaptopyridine 4-mercaptopyridine, the sodium salt of 2-mercaptopyridine-N-oxide, 2-mercaptobenzothiazole, and 4-methyl-4-H-1,2,4-triazole-3-thiol. Other preferred compounds include: 2-methylthiobenzothiazole, 2-thiohydantoin, methylenebisthiocyanate, L-cystin, and 4-R(thiazolidene-thione-4-carbonic acid).

In order for protection of the isothiazolone to be effective, the molar ratio of stabilizer to isothiazolone should preferably be at least 0.1:1, and most preferably at least 0.5:1. The minimum ratio generally depends on the aggressiveness of the system in which the isothiazolone is contained. A typical preferred range is from 0.5:1 to 1.5:1. However, some of the compounds which act as stabilizers may find other uses in the systems to which isothiazolones have been added—e.g., as microbicides in their own right. In such cases, stabilizer: isothiazolone molar ratios may be greater than 10:1.

Compositions of isothiazolone and stabilizer may additionally contain solvents. A suitable solvent will be any organic solvent which dissolves the isothiazolone, is compatible with the proposed end use, does not destabilize the isothiazolone, and does not react with the stabilizer to prevent its protective action.

Hydroxylic solvents, for example, polyols, such as glycols, alcohols and the like, may be used. In certain formulations, hydrocarbons, either aliphatic or aromatic, are useful solvents.

Preferred solvents are capped polyols, wherein the free hydroxyl group is replaced with an ether or ester function. Especially preferred are 2,5,8,11-tetraoxadodecane, commonly known as triethylene glycol dimethyl ether, and 4,7-dioxaundecanol-1-acetate, commonly known as diethylene glycol butyl ether acetate.

Water is a solvent for certain of the preferred isothiazolones and, the stabilizer may be employed in aqueous formulations.

In certain cases the stable adducts formed according to the invention may be in the form of a solid precipitate. This can generally be avoided by standard techniques for increasing the solubility product of a system such as adding emulsifiers, or diluting the system. Those skilled in the art will have little difficulty in altering the conditions to avoid precipitate formation if that should be a problem in any particular case.

It is known in the art that the performance of microbicides may be enhanced by combination with one or more other microbicides. Thus, other known microbicides may be combined advantageously with the compositions or compounds of this invention.

Uses of these protected isothiazolones may be at any locus subject to contamination by bacteria, fungi, yeast or algae. Typical loci are in aqueous systems such as water cooling, laundry rinse water, oil systems such as cutting oils, oil fields and the like where microorganisms need to be killed or where their growth needs to be controlled. However, they may also be used in all applications for which known microbicidal compositions are useful; preferred utilities of the compositions are to protect wood paint, adhesive, glue, paper, textile, leather, plastics, cardboard, lubricants, cosmetics, food, caulking, feed and industrial cooling water from microorganisms.

The following Examples are intended to illustrate the present invention. All percentages are by weight unless otherwise specified. Methods for quantitative determination of the isothiazolones in the following Examples in metal working fluids are described in detail in "Kathon ® 886 MW Microbicide and Kathon ® 893 MW Fungicide: Analysis in Metalworking Fluids by High-Performance Liquid Chromatography", 1988, Rohm and Haas Company.

EXAMPLE 1

This Example illustrates the protection afforded to isothiazolones by the stabilizers of the present invention.

Monoethanolamine is known to degrade isothiazolones when in contact with them in concentrated from. It is a component of metal working fluids, and is therefore a particular problem when present with isothiazolones in MWF concentrates.

In the following Example, a test system was used which comprised a 1:1 water/propylene glycol solvent, 10% monoethanolamine, 900 ppm of 2n-octyl-3-isothiazolone, and a stabilizer according to the invention. The system was maintained at 25° C., and the concentration of isothiazolone remaining after 1,2,4,8 and 12 weeks respectively was determined. Isothiazolone concentration was determined by removing an aliquot from the system at the appropriate time, diluting it 50-fold with a 1:1 water/propylene glycol solution, and then analysing for isothiazolone by HPLC.

Referring to Table 1, it should be noted that the initial concentration of isothiazolone in each case was 990 ppm. The subsequent readings are percentages of that value, and are accurate to ±5%.

tion for the isothiazolone. As a general rule, it is considered that useful stabilization is achieved if approximately 80% of the isothiazolone remains after 4 weeks, although when compared with the loss of isothiazolone with no stabilizer present, retention of 60% isothiazolone after 4 weeks may be considered to be effective stabilization.

EXAMPLE 2

Tests were also conducted on samples of two "synthetic" metal working fluid concentrates, two "semi-synthetic" MWF concentrates and one "emulsion" MWF concentrate. In all five cases, the stability of 2n-octyl-3-isothiazolone was compared with no stabilizer present, and with sodium omadine (sodium salt of

TABLE 1

| STABILIZER | STABILIZER CONCENTRATION (PPM) | % ISOTHIAZOLONE REMAINING (±5%) | | | | |
|---|---|---|---|---|---|---|
| | | 1 WK | 2 WKS | 4 WKS | 8 WKS | 12 WKS |
| None (control) | 0 | 72 | 0 | | | |
| Thiophenol (comparative) | 1000 | 0 | | | | |
| 2-mercapto ethane-sulfonic acid (comparative) | 1000 | 0 | | | | |
| Mercaptobenzothiazole | 1000 | 91 | 89 | 90 | 91 | 93 |
| | 500 | 98 | 91 | 0 | | |
| Na salt of 2-mercapto-pyridine N-oxide | 2000 | 100 | 100 | 100 | 94 | 97 |
| | 800 | 96 | 98 | 89 | 81 | n/a |
| | 400 | 78 | 0 | | | |
| 2-mercaptopyridine | 1000 | 88 | 85 | 81 | 76 | 69 |
| 4-mercaptopyridine | 1000 | 91 | 91 | 92 | 84 | 81 |
| Benzothiazole | 1000 | 95 | 87 | 78 | 69 | n/a |
| 2-thiohydantoin | 1000 | 99 | 96 | 94 | 95 | 95 |
| L-cystin | 1000 | 100 | 99 | 100 | 100 | 100 |
| Methylene bis-thiocyanate | 1000 | 100 | 100 | 98 | 100 | 100 |
| 2-methylthiobenzothiazole | 1000 | 99 | 99 | 98 | n/a | 93 |
| 4-methyl 4-H-1,2,4, triazole-3-thiol | 1000 | 100 | 100 | 96 | 98 | 100 |
| 4-R-(thiazolidinethione)-4-carbonic acid | 1000 | 100 | 99 | 94 | 98 | 54 |
| 2-mercaptopyrimidine | 1000 | 96 | 97 | 88 | 64 | 44 |

Referring to Table 1, it can be seen that with no stabilizer present the isothiazolone is rapidly decomposed by the monoethanolamine, having completely disappeared within two weeks. In the cases of the two comparative examples, it is believed that these are instances where formation of the isothiazolone-stabilizer adduct is irreversible: thus when the aliquot for analysis is diluted 50-fold the isothiazolone is not released by hydrolysis, but instead remains as part of the adduct, therefore being neither detectable nor microbicidally active.

The present invention is limited to those sulphur-containing compounds which reversibly form adducts with the isothiazolone. As can be seen from the remaining examples in Table 1, these provide exceptional protec- 2-mercaptopyridine-N-oxide) present.

MWF concentrates A and B were "synthetic" types, containing in addition to oils and water amines, synthetic esters, solubilisers, coupling agents, anti-corrosion agents and extreme pressure agents. MWF concentrates C and D were "semi-synthetic" types, similar in composition to the synthetic oils but with no synthetic esters, and additionally containing lubricating oils and emulsifiers. MWF concentrate E was an "emulsion" type.

Analysis of the isothiazolone content in each case was carried out as in Example 1, with an error margin of ±5%. In every case, the amount of isothiazolone present was 1,000 ppm; the amount of sodium omadine present is given.

TABLE 2

| MWF CONCENTRATE | SODIUM OMADINE (PPM) | % ISOTHIAZOLONE REMAINING (±5%) | | | | |
|---|---|---|---|---|---|---|
| | | 1 WK | 2 WKS | 4 WKS | 8 WKS | 12 WKS |
| A | None | 0 | | | | |
| | 1000 | 96 | 91 | 88 | 88 | 86 |
| B | None | 0 | | | | |
| | 1000 | 83 | 75 | 67 | 65 | 62 |
| C | None | 0 | | | | |
| | 1000 | 97 | 92 | 91 | 89 | 89 |
| D | None | 0 | | | | |
| | 1000 | 96 | 94 | 92 | 92 | 91 |
| E | None | 62 | 0 | | | |
| | 1000 | 97 | — | 100 | — | 100 |
| | 500 | 97 | — | 99 | 100 | 97 |

This Table clearly shows the dramatic effect of the stabilizer on the isothiazolone presence. In the case of MWF concentrate E, it shows that when the components of a system are less aggressive towards the isothiazolone, a much smaller amount of stabilizer can successfully provide excellent protection.

I claim:

1. A method of protecting against chemical degradation an isothiazolone of the formula:

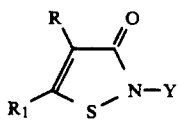

wherein

Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloaklylamino, carbamoxy, or isothiazolonyl; an unsubstituted or halo-substituted $(C_2-C_8)$ alkenyl or alkynyl; a $(C_7-C_{10})$aralkyl optionally substituted with one or more of halogen, $(C_1-C_4)$alkyl or $(C_1-C_4)$alkoxy; or an aryl optionally substituted with one or more of halogen, nitro, $(C_1-C_4)$alkyl, $(C_1-C_4)$alkyl-acylamino, carb$(C_1-C_4)$alkoxy or sulfamyl; and R and $R^1$ are each independently H, halogen, $(C_1-C_4)$ alkyl, $(C_4-C_8)$ cycloalkyl or joined together to form a phenyl; comprising incorporating therewith an organic sulphur-containing compound, or an alkaline metal or amine salt thereof, capable of forming an adduct with said isotiazolone which is reversible upon hydrolysis, said sulfur-containing compound being selected from the group consisting of mercaptobenzothiazole, the sodium salt of 2-mercaptopyridine-N-oxide, 2-mercaptopyridine, 4-mercaptopyridine, benzothiazole, 2-thiohydantoin, L-cystin, methylenebis-thiocyante, 2-methylthiobenzothiazole, 4-methyl 4-H-1,2,4-triazole-3-thiol, 4-R-(thiazolidinethione)-4-carbonic acid, and 2-mercaptopyrimidine.

2. Method according to claim 1, wherein the protection of the isothiazolone is subsequently terminated by decomposition of said adduct to release the isothiazolone by hydrolysis of the adduct.

3. Method according to claim 2, wherein the isothiazolone is protected whilst in a metal working fluid concentrate, and released by hydrolysis of the adduct upon dilution of the concentrate.

4. Method according to claim 1, wherein Y is $(C_1-C_{18})$ alkyl or $(C_3-C_{12})$ cycloalkyl; R is H or Me; and $R^1$ is H.

5. Method according to claim 4 wherein the isothiazolone is 2-methyl-3-isothiazolone or 2-n-octyl-3-isothiazolone.

6. Method according to claim 1 wherein R and $R^1$ are each independently H, $(C_1-C_4)$ alkyl, $(C_4-C_8)$ cycloalkyl or joined to form a phenyl, and the sulphur-containing compound is a mercaptan or salt thereof, preferably a nitrogen-based heterocyclic thiol or salt thereof.

7. Method according to claim 1 wherein said sulfur-containing compound is a nitrogen-based heterocyclic thiol or salt thereof.

8. Composition comprising an adduct of
(A) an isothiazolone of the formula:

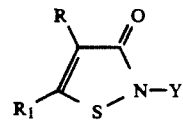

wherein

Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloaklylamino, carbamoxy, or isothiazolonyl; an unsubstituted or halo-substituted $(C_2-C_8)$ alkenyl or alkynyl; a $(C_7-C_{10})$aralkyl optionally substituted with one or more of halogen, $(C_1-C_4)$alkyl or $(C_1-C_4)$alkoxy; or an aryl optionally substituted with one or more of halogen, nitro, $(C_1-C_4)$alkyl, $(C_1-C_4)$alkyl-acylamino, carb$(C_1-C_4)$alkoxy or sulfamyl; and R and $R^1$ are each independently H, halogen, $(C_1-C_4)$ alkyl, $(C_4-C_8)$ cycloalkyl or joined together to form a phenyl; and (B) organic sulphur-containing compound, or alkaline metal or amine salt thereof, capable of forming an adduct with said isothiazolone, said adduct being reversible upon hydrolysis, said sulfur-containing compound being selected from the group consisting of mercaptobenzothiazole, the sodium salt of 2-mercaptopyridine-N-oxide, 2-mercaptopyridine, 4-mercaptopyridine, benzothiazole, 2-thiohydantoin, L-cystin, methylenebisthiocyante, 2-methylthiobenzothiazole, 4-methyl 4-H-1,2,4-triazole-3-thiol, 4-R-(thiazolidinethione)-4-carbonic acid, and 2-mercaptopyrimidine.

9. Composition according to claim 8 wherein the molar ratio of sulphur-containing compound to isothiazolone is at least 0.1:1.

10. Composition according to claim 8 wherein the molar ratio of sulphur-containing compound to isothiazolone is at least 0.5:1.

* * * * *